US008563251B2

(12) United States Patent
Rohwer et al.

(10) Patent No.: US 8,563,251 B2
(45) Date of Patent: Oct. 22, 2013

(54) HIGH-THROUGHPUT METHODS FOR QUANTIFYING CELLS IN ENVIRONMENTAL AND LABORATORY SAMPLES

(75) Inventors: Forest Rohwer, San Diego, CA (US); Linda Wegley, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 841 days.

(21) Appl. No.: 12/300,628

(22) PCT Filed: May 11, 2007

(86) PCT No.: PCT/US2007/068813

§ 371 (c)(1),
(2), (4) Date: Dec. 11, 2009

(87) PCT Pub. No.: WO2008/060687

PCT Pub. Date: May 22, 2008

(65) Prior Publication Data

US 2010/0167276 A1     Jul. 1, 2010

Related U.S. Application Data

(60) Provisional application No. 60/800,078, filed on May 12, 2006.

(51) Int. Cl.
*C12Q 1/68* (2006.01)

(52) U.S. Cl.
USPC .................. 435/6.15; 435/7.32; 435/40.51

(58) Field of Classification Search
None
See application file for complete search history.

(56) References Cited

U.S. PATENT DOCUMENTS

| | | | |
|---|---|---|---|
| 4,225,783 A | 9/1980 | Palin et al. | |
| 6,190,870 B1 * | 2/2001 | Schmitz et al. | 435/7.23 |
| 6,255,118 B1 | 7/2001 | Alfano et al. | |
| 6,426,505 B1 | 7/2002 | Rao et al. | |
| 6,563,585 B1 | 5/2003 | Rao et al. | |
| 6,806,455 B2 | 10/2004 | Zarate et al. | |
| 6,852,986 B1 | 2/2005 | Lee et al. | |
| 2002/0119450 A1 | 8/2002 | Lee et al. | |
| 2002/0168630 A1 * | 11/2002 | Fleming et al. | 435/5 |
| 2003/0215892 A1 | 11/2003 | Valle et al. | |
| 2003/0219850 A1 | 11/2003 | Tsuji et al. | |

OTHER PUBLICATIONS

Tuma R.S. et al., Characterization of SYBR Gold Nucleic Acid Gel Stain: A Dye Optimized for Use with 300-nm Ultraviolet Transilluminators, Analytical Biochemistry, 1999, vol. 268, pp. 278-288.*
Kan J. et al., Metaproteomic analysis of Chesapeake Bay microbial communities, Saline Systems, Aug. 19, 2005, vol. 1, No. 7, pp. 1-13 (BioMed Central Open access online publication).*
Agusti S. et al., Cell viability in natural phytoplankton communities quantified by a membrane permeability probe, Limnol. Oceanogr., 2002, vol. 47, No. 3, pp. 818-828.*
Janecki A. et al., Experimental pitfalls in evaluating vectorial protein secretion in vitro; Sertoli cell secretion of androgen-binding protein and transferrin in two-compartment culture chambers, In Vitro Cell Dev. Biol., Jun. 1988, vol. 24, No. 6, pp. 518-524.*
Cortese J., At the Speed of Light, The Scientist Magazine, Jul. 10, 2000, pp. 1-5, publication at the web at : http://classic.the-scientist.com/?articles.view/articleNo/12927; accessed on Oct. 13, 2012.*
U2: theLabRat.com—2005: Protocol for CyQUANT™ Cell Proliferation Assay, pp. 1-5; an online publication at the web at http://www.thelabrat.com/protocols/cellproliferation.shtml; accessed on Oct. 10, 2012.*
V2: Fuller M. E. et al., Development of a Vital Fluorescent Staining Method for Monitoring Bacterial Transport in Subsurface Environments, Applied and Environmental Microbiology, Oct. 2000, vol. 66, No. 10, pp. 4486-4496.*
W2: Wegley L. et al. Rapid estimation of microbial numbers in water using bulk fluorescence, Environmental Microbiology, 2006, vol. 8, No. 10, pp. 1775-1782.*
International Preliminary Report on Patentability Chapter-I PCT/US2007/68813, mailed on Aug. 12, 2008.
International Search Report (ISR) PCT/US2007/68813, published as WO2008-060687-A3, mailed on Aug. 12, 2008.
Written opinion of ISA PCT/US2007/68813, mailed on Aug. 12, 2008.
Boehme, J., et al, "Viruses, bacterioplankton, and phytoplankton in the southeastern Gulf of Mexico: distribution and contribution to oceanic DNA pools," Marine Ecology Progress Series (1993) vol. 97:1-10.
Breitbart, Mya, et al., "Phage Community Dynamics in Hot Springs," Applied and Environmental Microbiology, Mar. 2004, p. 1633-1640, vol. 70, No. 3.
Deflaun, Mary, et all, "Distribution and molecular weight of dissolved DNA in subtropical estuarine and oceanic environments," Marine Ecology Progress Series (1987) vol. 38:65-73.
Gasol, Josep, et al., "Significance of Size and Nucleic Acid Content Heterogeneity as Measured by Flow Cytometry in Natural Planktonic Bacteria," Applied and Environmental Microbiology, Oct. 1999, p. 4475-4483, vol. 65, No. 10.
Guatelli, John, et al., "Isothermal, in vitro amplification of nucleic acids by a multienzyme reaction modeled after retroviral replication", PNAS Mar. 1, 1990 vol. 87 No. 5 1874-1878.
Hobbie, J.E., et al., "Use of nuclepore filters for counting bacteria by fluorescence microscopy," Appl Environ Microbiol. May 1977; 33(5): 1225-1228.
Jiang, Sunny, et al., "Viral Contribution to Dissolved DNA in the Marine Environment as Determined by Differential Centrifugation and Kingdom Probing," Appl. Environ. Microbiol., Jan. 1995, 317-325, vol. 61, No. 1.
Kwoh, D.Y., et al., "Transcription-based amplification system and detection of amplified human immunodeficiency virus type 1 with a bead-based sandwich hybridization format," PNAS Feb. 1, 1989 vol. 86 No. 4 1173-1177.
Noble, Rachel, et al., "Use of SYBR Green I for rapid epifluorescence counts of marine viruses and bacteria" Aquat Microb Ecol 14: 113-118. 1998.
Paul, John, et al. "Dynamics of extracellular DNA in the marine environment," Appl Environ Microbiol. Jan. 1987; 53(1): 170-179.
Smith, J.H., et al., "Detection of *Streptococcus pneumoniae* in sputum samples by PCR," J. Clin. Microbiol. May 1994; 32(5): 1308-1311.
Smith, J.H., et al., "Detection of Mycobacterium tuberculosis directly from sputum by using a prototype automated Q-beta replicase assay," Journal of Clinical Microbiology, Jun. 1997, 1477-1483, vol. 35, No. 6.
Molecular Probes—Invitrogen catalog for SYBR® Gold Nucleic Acid Gel Stain, Apr. 24, 2006.
Chen, F., et al., "Application of Digital Image Analysis and Flow Cytometry To Enumerate Marine Viruses Stained with SYBR Gold," APplied and Environmental Microbiology, Feb. 2001, p. 539-545, vol. 67, No. 2.

* cited by examiner

*Primary Examiner* — Sandra Saucier
*Assistant Examiner* — Satyendra Singh
(74) *Attorney, Agent, or Firm* — Gregory P. Einhorn; Gavrilovich, Dodd & Lindsey LLP

(57) ABSTRACT

The invention provides compositions (e.g., kits) and methods for determine the number of bacteria and other microbes in samples having low concentrations of microbes, for use, e.g., in biological warfare defense, microbe detection and agricultural and environmental sciences.

13 Claims, 10 Drawing Sheets

HIGH-THROUGHPUT METHODS FOR QUANTIFYING CELLS IN ENVIRONMENTAL AND LABORATORY SAMPLES

FEDERAL FUNDING

This invention was produced in part using funds from the Federal government under a DOD Grant as a SPAWAR Systems Center San Diego Independent Research (IR) Program and a National Science Foundation Aquatic Phage Grant NSF03-16518. Accordingly, the Federal government has certain rights in this invention.

FIELD OF THE INVENTION

This invention related generally to biological warfare defense, microbe detection and agricultural and environmental sciences. In particular, the invention provides compositions (e.g., kits) and methods, including high-throughput methods, for determining the number of (enumerating) bacteria and other microbes in samples (such as environmental samples) having low concentrations of microbes.

SUMMARY OF THE INVENTION

The compositions and methods of the invention can determine the number of bacteria and other microbes in samples having low concentrations of microbes. Thus, the invention can be effectively used on environmental samples where microbe presence or abundance needs to be monitored. For example, the methods of the invention can be practiced for research, agricultural or biodefense purposes, e.g., to detect trace quantities of microbes, e.g., pathogens, biological warfare agents (anthrax) and the like.

In one aspect, the compositions and methods of the invention provide high-throughput methods for quickly quantifying the number of microbial cells in environmental or laboratory samples where the concentrations are approximately $<10^7$, or $<10^6$, or $<10^5$ cells per ml. In one aspect, the protocols and devices of the invention are mobile and can easily be taken into the field, e.g., as biological warfare detection agents.

In one aspect, the compositions and methods of the invention provide high-throughput methods applicable in several fields, including biological warfare defense, water quality assessment, aquaculture, microbial ecology, and the like. Exemplary devices of the invention are useful for routine monitoring of aquaculture tanks, storm drains in a city, or anywhere else that microbial numbers need to be rapidly and routinely determined.

The invention provides methods for enumerating (counting) microbial cells in a sample, the method comprising the following steps: (a) providing a liquid or water sample, and optionally, if appropriate, making a solution comprising an initial non-liquid sample (e.g., adding a solution to a soil sample, or liquefying a tissue sample); (b) filtering the liquid or water sample with at least one low protein binding filter; (c) adding SYBR® Gold nucleic acid stain, or equivalent; (d) measuring the total fluorescence, thereby enumerating (counting) microbial cells in the sample.

In one aspect, the sample is an environmental sample, for example, a biological, soil, air or water sample. The water sample can comprise water from a salt water, hot spring, public water supply, water tank, reservoir, fresh water, aquifer, storm drain, river, lake or aquaculture pond water source. The biological sample can comprise a plant, seed or an animal tissue sample.

In one aspect, the low protein binding filter comprises a polycarbonate filter, a polyvinylidenedifluoride (PVDF) filter or equivalent, e.g., the polyvinylidenedifluoride (PVDF) filter comprises a FLUORODYNE II® hydrophilic PVDF filter (Pall Corporation, East Hills, N.Y.), a DURAPORE® PVDF filter (Millipore, Billerica, Mass.) or a POLYLINE™ PVDF filter (Hayward Filtration, Elizabeth, N.J.).

In one aspect, the method of claim 1, wherein the at least one low protein binding filter is a 0.30 µm filter, 0.35 µm filter, 0.40 µm filter, 0.45 µm filter, a 0.50 µm filter or a 0.55 µm filter.

In one aspect, the liquid or water sample is diluted before filtering, after filtering or both before and after filtering. The liquid or water sample can be treated with a DNase I before filtering, after filtering or both before and after filtering, or before dilution, after dilution or both before and after dilution.

In one aspect, the total fluorescence and/or "relative fluorescent units" (RFU) is measured with a fluorescent spectrophotometer.

The invention provides kits comprising the solutions for practicing any of the methods of the invention, and optionally the kit further comprises instructions for practicing any of the methods of the invention.

The invention provides multiplexed high through-put systems for enumerating (counting) microbial cells in a sample as set forth in the methods of this invention, comprising at least one sample holding/mixing unit, at least one low protein binding filter for filtering the samples, an injection unit for injecting into the mixing unit the SYBR® Gold nucleic acid stain, a sample processor for inputting samples into the fluorometer, a fluorometer and a data recorder. In one aspect, the multiplexed high through-put system further comprises an injection unit for adding DNase I into a mixing unit. In one aspect, the multiplexed high through-put system further comprises a computer system and data output device for calculating and outputting to a user total fluorescence and/or "relative fluorescent units" (RFU). Any fluorometer or fluorometer system can be used to practice this invention, see, e.g., U.S. Pat. Nos. 6,852,986; 6,806,455; 6,563,585; 6,426,505; 6,255,118.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

Like reference symbols in the various drawings indicate like elements.

DETAILED DESCRIPTION

Figure 1A:
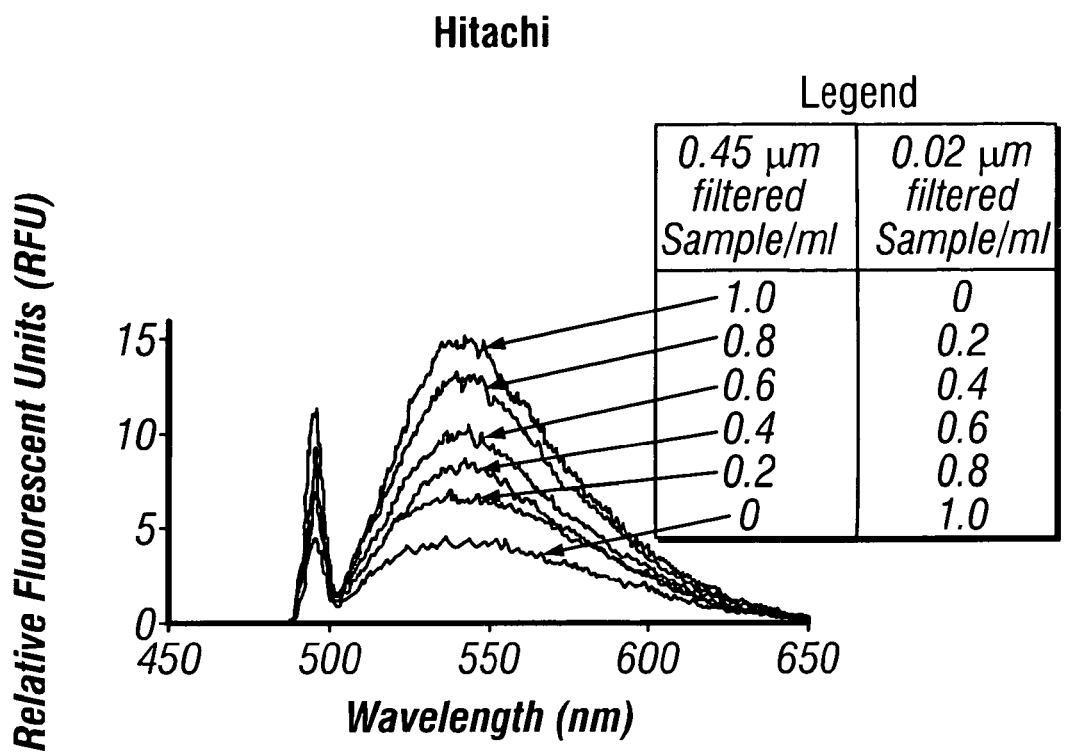
FIG. 1A illustrates a "scanner plot" summarizing data from a measurement of bulk fluorescence in a seawater dilution series using a fluorometer.
Figure 1B:
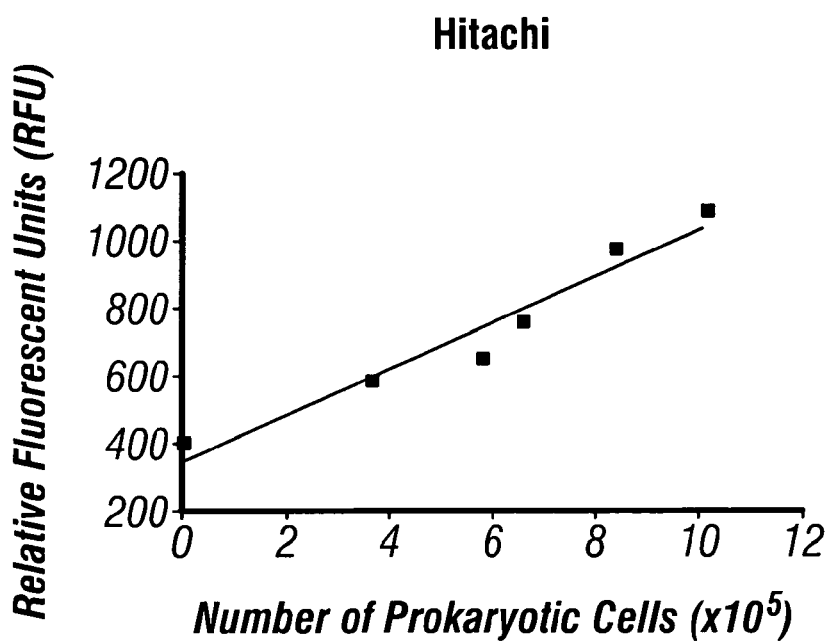
FIG. 1B illustrates a graphic representation of the correlation between bulk fluorescence and direct cell counts.

The invention provides compositions and methods for the enumeration of microbial cells without culturing. The compositions and methods of the invention can be used for microbial ecology and/or water quality evaluation. The invention utilizes bulk fluorescence using the SYBR® Gold (Invitrogen-Molecular Probes, Eugene Oreg.) DNA stain, or equivalent, to rapidly estimate microbial numbers in an environmental sample, a soil or water environment, including, e.g., a fresh, marine, and/or estuarine water environmental sample.

The bulk fluorescence method of the invention is comparable to estimating cell concentrations in cultures using optical density. The enhanced method of the invention enables the user to estimate microbial numbers at low concentration, e.g., the concentrations found in an environmental sample. The methods of the invention work in both single-cell and 96-well plate fluorescent spectrophotometers.

In practicing the invention, differences of approximately $10^5$ cells per ml were discernable and the precision of the bulk fluorescence was higher than direct counting by epifluorescent microscopy.

In one aspect, treatment with DNase I is used, it increases sensitivity by lowering background noise attributed to free DNA. This embodiment of the invention is a simple, rapid, inexpensive technique which is adaptable for automatically estimating microbial numbers in samples.

In practicing the invention, amplification reactions can be used to quantify the amount of nucleic acid in a sample, label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., *PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) Proc. Natl. Acad. Sci. USA 86:1173); and, self-sustained sequence replication (see, e.g., Guatelli (1990) *Proc. Natl. Acad. Sci.* USA 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; and Sooknanan (1995) *Biotechnology* 13:563-564.

The invention will be further described with reference to the invention described in the following appendix; however, it is to be understood that the invention is not limited to such examples.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the claims.

Example 1

Enumeration of microbial cells without culturing is an essential technique for microbial ecology and water quality evaluation. Here we show that bulk fluorescence using the SYBR Gold DNA stain can be used to rapidly estimate microbial numbers in fresh, marine, and estuarine waters. The bulk fluorescence method is comparable to estimating cell concentrations in cultures using optical density, however, this enhanced method enables the user to estimate microbial numbers at lower concentration and found in environmental samples. The technique worked in both single-cell and 96-well plate fluorescent spectrophotometers. Differences of $\sim 10^5$ cells per ml were discernable and the precision of the bulk fluorescence was higher than direct counting by epifluorescent microscopy. Treatment with DNase I increased sensitivity by lowering background noise attributed to free DNA. This technique is simple, rapid, inexpensive, and adaptable for automatically estimating microbial numbers in water samples.

Introduction

A major breakthrough in microbial ecology was direct counting of microbial cells via DAPI staining and epifluorescence microscopy (Hobbie et al., 1977). Using this method, it was established that there are $\sim 10^6$ prokaryotic cells per milliliter of seawater and $\sim 10^9$ prokaryotic cells per gram of soil or sediment, despite the fact that only 1% of these cells are readily culturable.

Direct count protocols have been modified to incorporate newer nucleic acid stains, such as SYBR Green (Noble and Fuhrman, 1998) and SYBR Gold (Breitbart et al., 2004). The SYBR dyes have a greater fluorescence enhancement (i.e., increase in fluorescence when the dye binds to DNA) than ethidium bromide or DAPI. SYBR nucleic acid stains also have a higher fluorescence quantum yield, making them more sensitive. These characteristics have made the direct counts of prokaryotic cells, and even viruses, relatively routine (Noble and Fuhrman, 1998). Further improvements have included the adaptation of flow cytometry and automated image analyses software.

Despite these improvements, current methods for counting microbes are relatively slow and require expensive/sophisticated equipment (e.g., flow cytometers or epifluorescent microscopes). An inexpensive, rapid technique for estimating microbial concentrations would be valuable to investigators in several fields including water quality assessment, aquaculture, and microbial ecology. Here, we present a rapid method for estimating microbial numbers in marine, estuarine, and fresh water samples using simple fluorometry and the nucleic acid stain SYBR Gold.

Results and Discussion

Figures 1, 4:
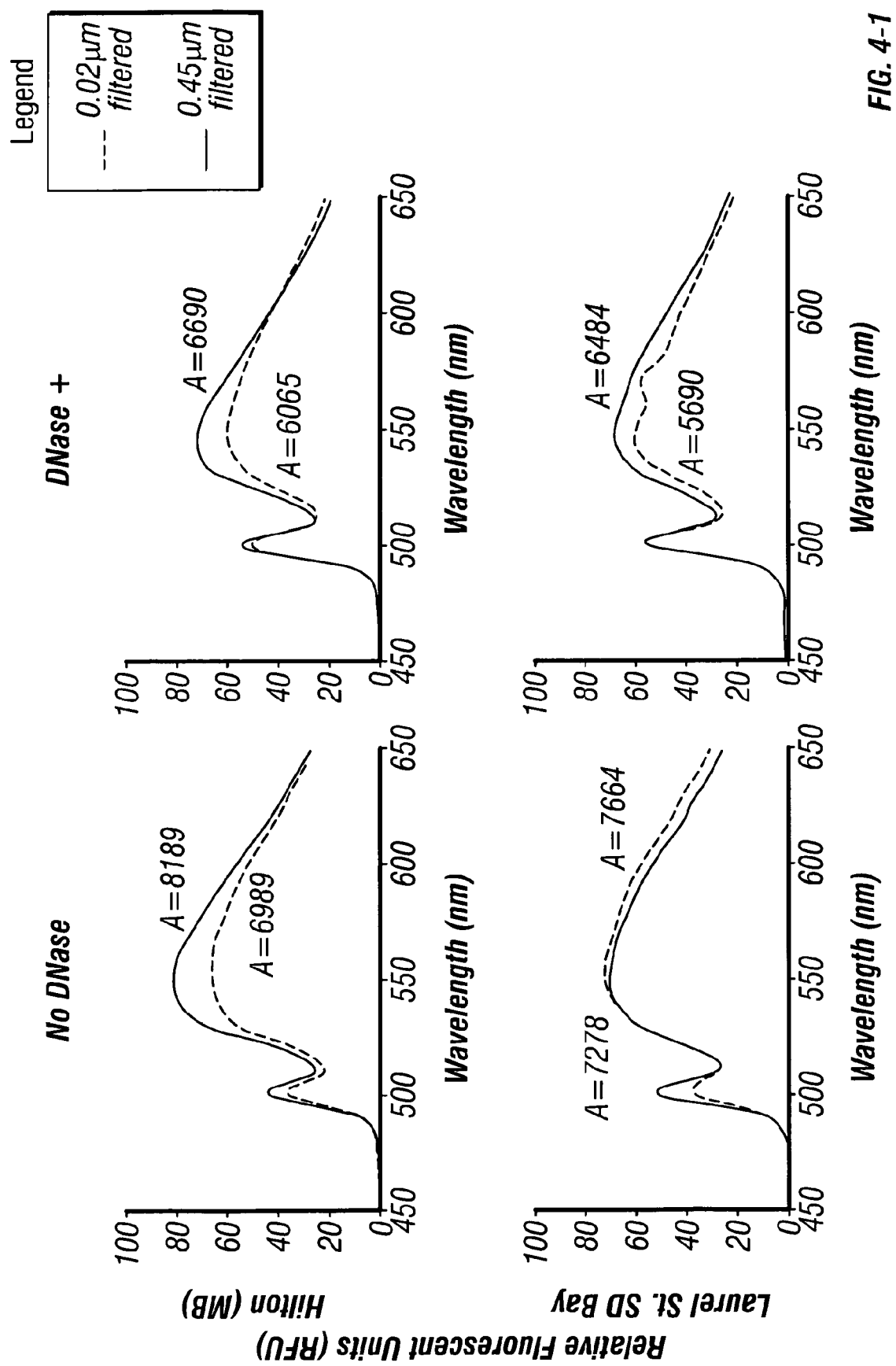
FIG. 4 graphically illustrates the data showing the effects of DNase I on the relative fluorescence of various water samples, as described in detail in Example 1, below.
Figures 2, 4:
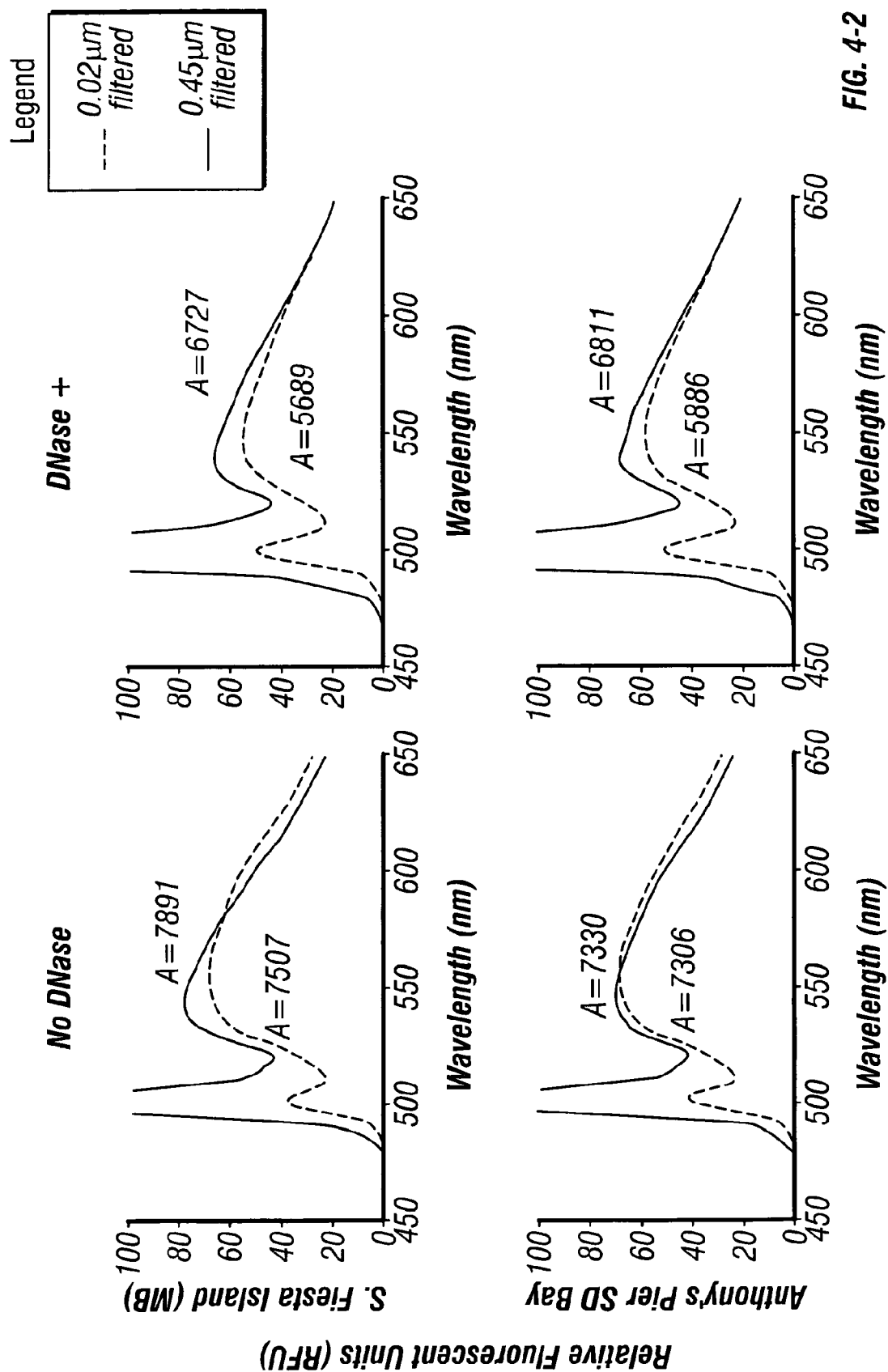
Figures 3, 4:
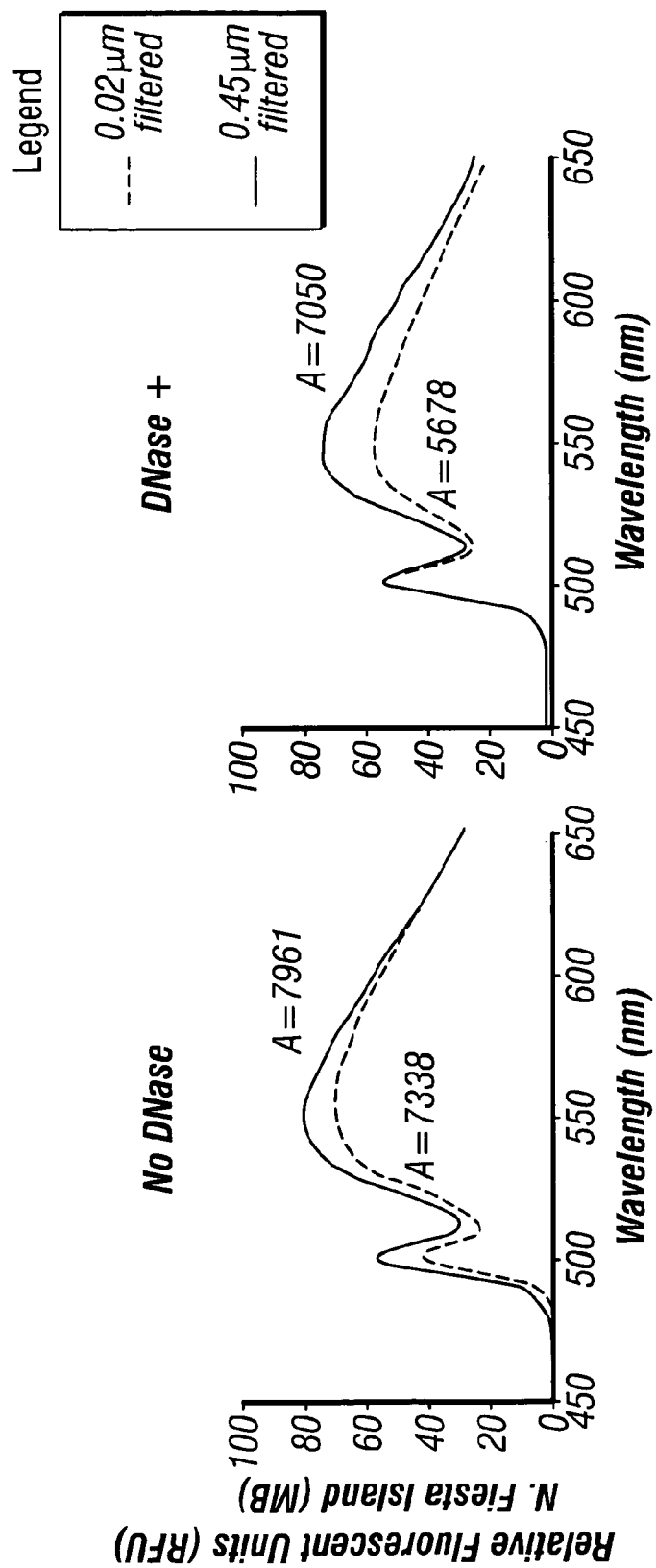

Correlation of Microbial Numbers to SYBR® Gold Bulk Fluorescence: To determine if bulk fluorescence could be used to quantify microbes, a dilution series was created using varying proportions of 0.45 μm (+microbes) and 0.02 μm filtered seawater (-microbes). The different dilutions were stained with SYBR® Gold and the Relative Fluorescence Units (RFUs) measured on a Hitachi f4500™ fluorometer. As shown in FIG. 1A, there was a correlation between the dilutions and bulk SYBR Gold fluorescence. There was also a strong correlation (r.sup.2=0.94) between the relative fluorescence as measured by the fluorometer and the number of microbes in the samples, which were counted manually using epifluorescence microscopy (FIG. 1 B).

Figure 1C:
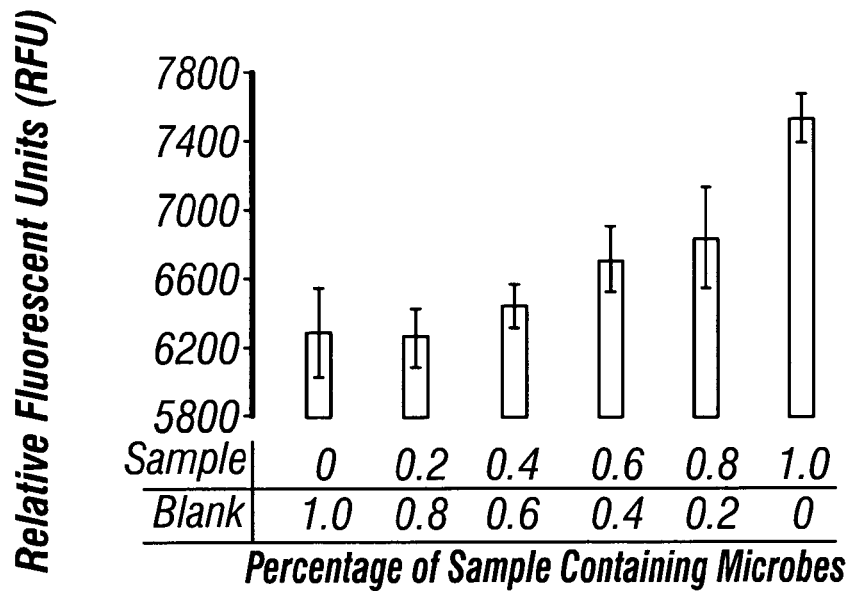
FIG. 1C graphically illustrates data from a measurement of bulk fluorescence in a seawater dilution series using a fluorometer.
Figure 1D:
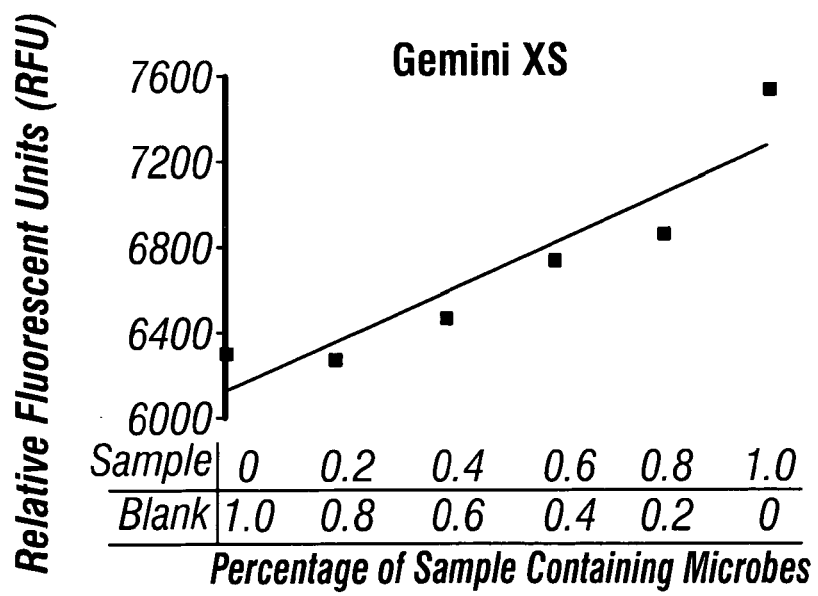
FIG. 1D illustrates a graphic representation of the correlation between relative fluorescence and percentage of whole seawater in a sample; as described in detail in Example 1, below.

A similar dilution series was also measured on the Gemini XS 96-well fluorometer. There were significant differences ($p<0.05$) between 0.45 μm samples diluted by 40% with 0.02 μm filtered seawater (e.g., 20% vs 60% and 60% vs 100% in FIG. 1C). The $r^2$ value for the seawater dilution series measured on the Gemini fluorometer was 0.86 (FIG. 1D). These preliminary analyses suggested that bulk fluorescence with SYBR Gold may be used to enumerate microbes on both single-cell and multi-well fluorometers.

Figure 2:
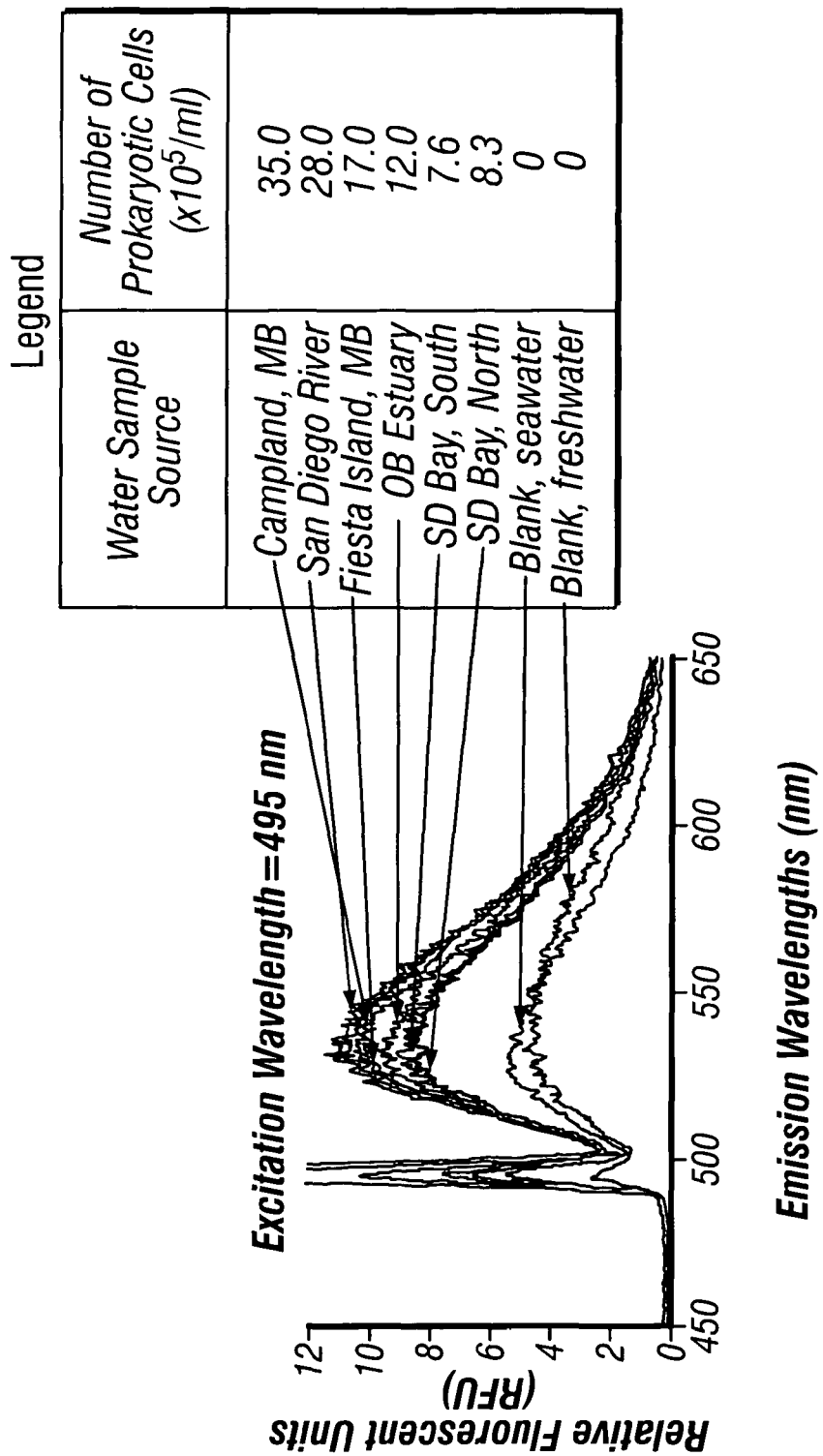
FIG. 2 illustrates measurement of bulk fluorescence in various water samples using a spectrophotometer, as described in detail in Example 1, below.

Microbial Numbers in Environmental Water Samples: Bulk fluorescence and direct counts were performed on fresh, marine, and estuarine water samples collected from the San Diego area. As shown in FIG. 2, there were visibly discernable differences between samples that vary by at least $5\times10^5$ cells $ml^{-1}$.

Figure 3:
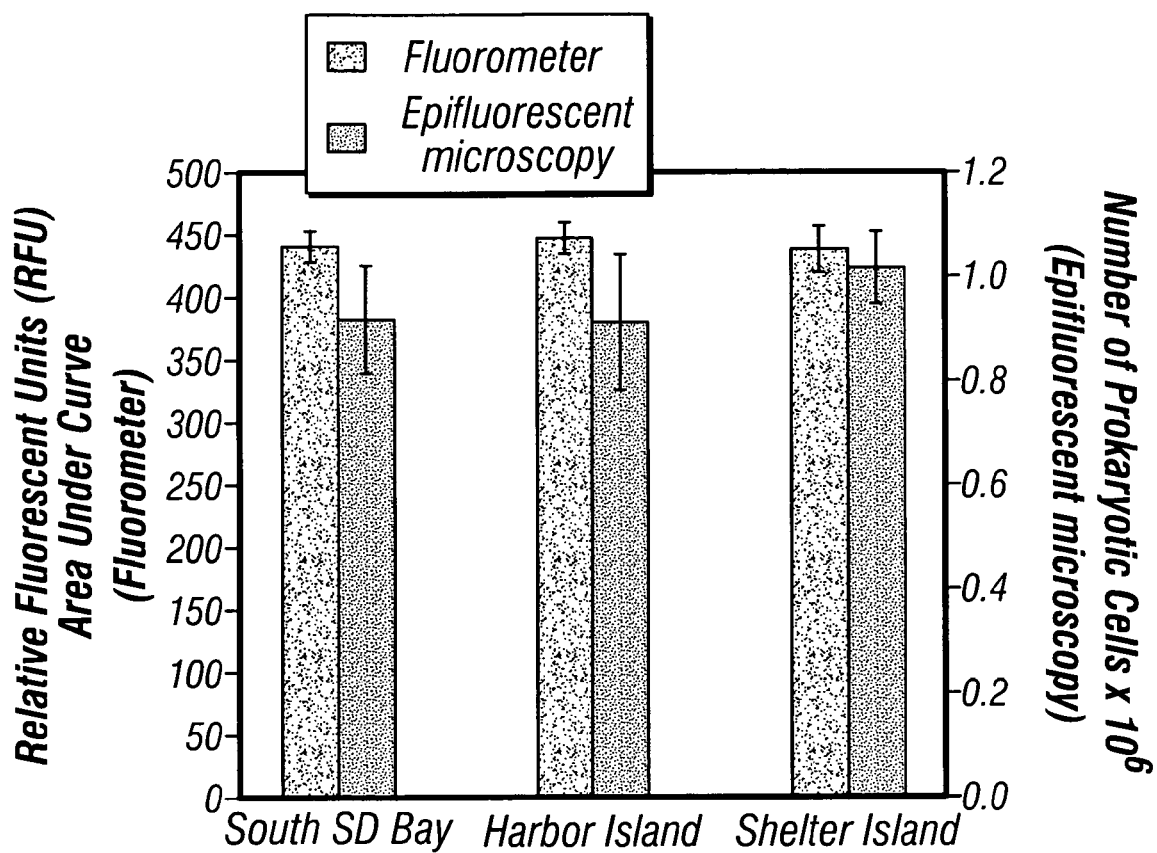
FIG. 3 graphically illustrates the precision of measurement of relative fluorescence in various water samples using a spectrophotometer and epifluorescent microscopy, as described in detail in Example 1, below.

Precision: The precision of the bulk fluorescence method versus direct counts was compared in three water samples. The error between samples was estimated using the standard deviation of the mean from the three replicate samples measured per site. The standard deviation in RFUs for the three Samples ranged from 12 to 18 (FIG. 3). Estimates of total bacterial numbers using epifluorescent microscopy ranged from $9.1\times10^5$ to $1.0\times10^6$ and the standard deviation ranged from $7.2\times10^4$ to $1.3\times10^5$ (FIG. 3). In the South San Diego Bay water sample, error with the fluorometer was 2.8% and error with manual counting was 12%; in the Harbor Island sample, error with fluorometer was 2.9% and error with manual counting was 15%; and in the Shelter Island sample, error with fluorometer was 4.2% and error with manual counting was 7.1%. Therefore, the precision was higher with the fluorometer then with manually counting using epifluorescent microscopy.

Treatment with DNase I Lowers Background and Increases Sensitivity: Dissolved DNA has been found at concentrations as high as 5-44 $\mu gl^{-1}$. in estuaries and 2-15 $\mu gl^{-1}$ for coastal oceanic environments (DeFlaun et al., 1987; Paul et al., 1987; Boehme et al., 1993; Jiang and Paul, 1995). Therefore, it is likely that dissolved DNA will cause background noise in the bulk fluorescence signal. To test this, 5 water samples were treated with DNase I and assayed with the bulk fluorescence protocol. The addition of the DNase I lowered background noise associated with the Blank (FIG. 4). For example, the signal in the Anthony's Pier, Laurel St., and South Fiesta Island samples was completely masked by the free DNA noise. Therefore, we recommend that a DNase I step be included when using this method. The SYBR® Gold and DNase I can be added simultaneously (data not shown).

Figures 1, 5:
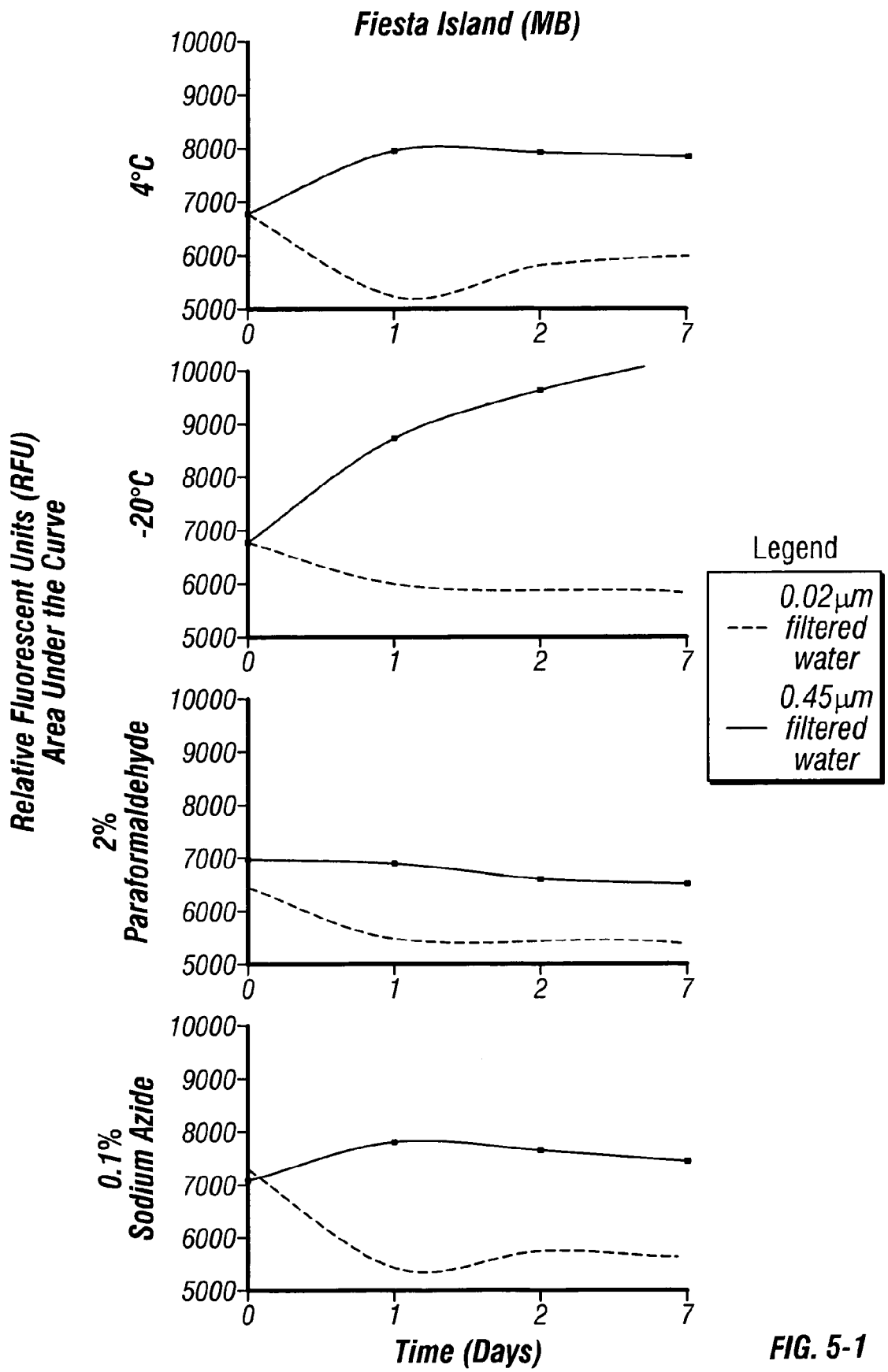
FIG. 5 graphically illustrates the data showing the effects of preservatives on the relative fluorescence of various water samples, as described in detail in Example 1, below.
Figures 2, 5:
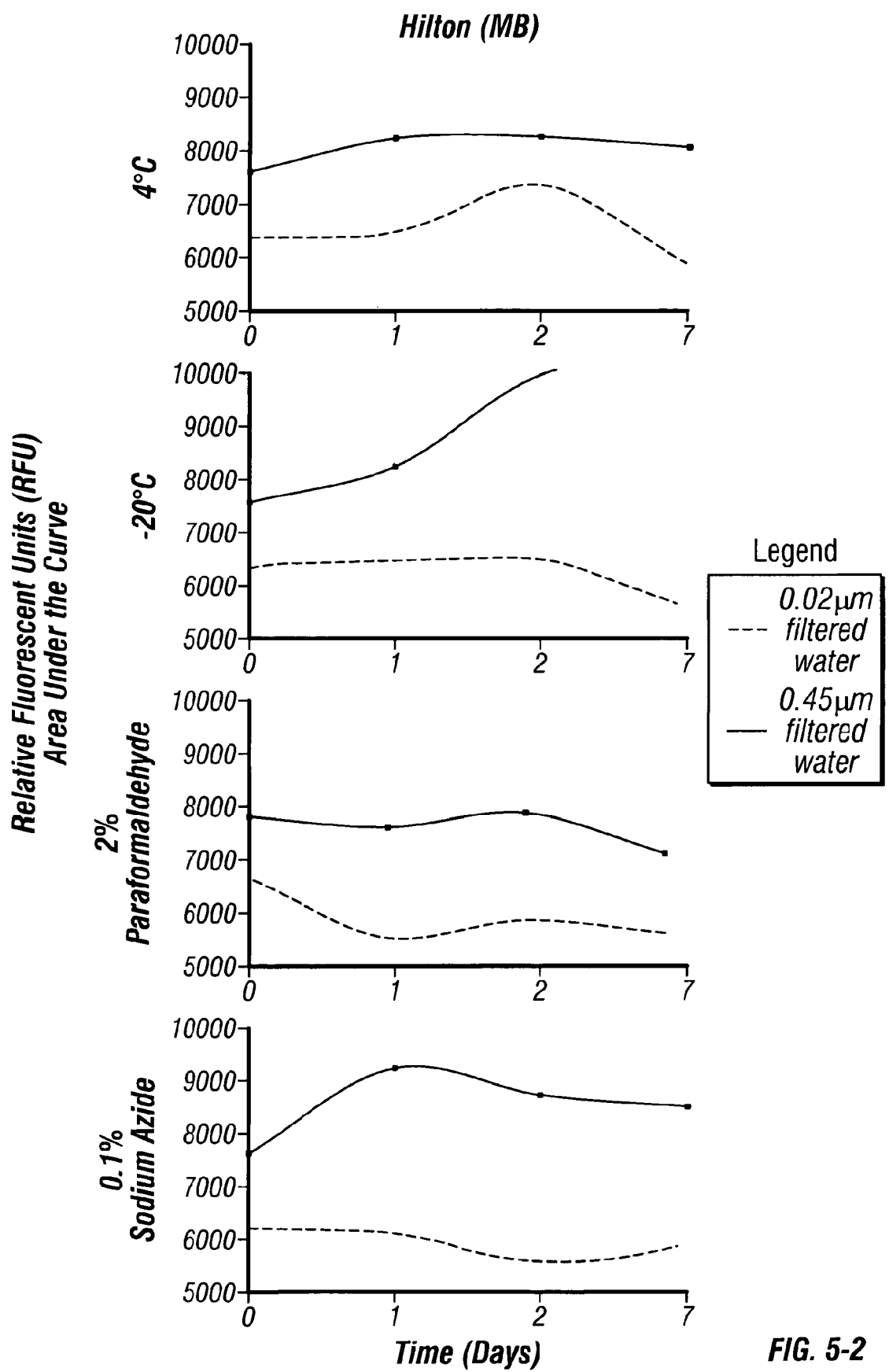
Figures 3, 5:
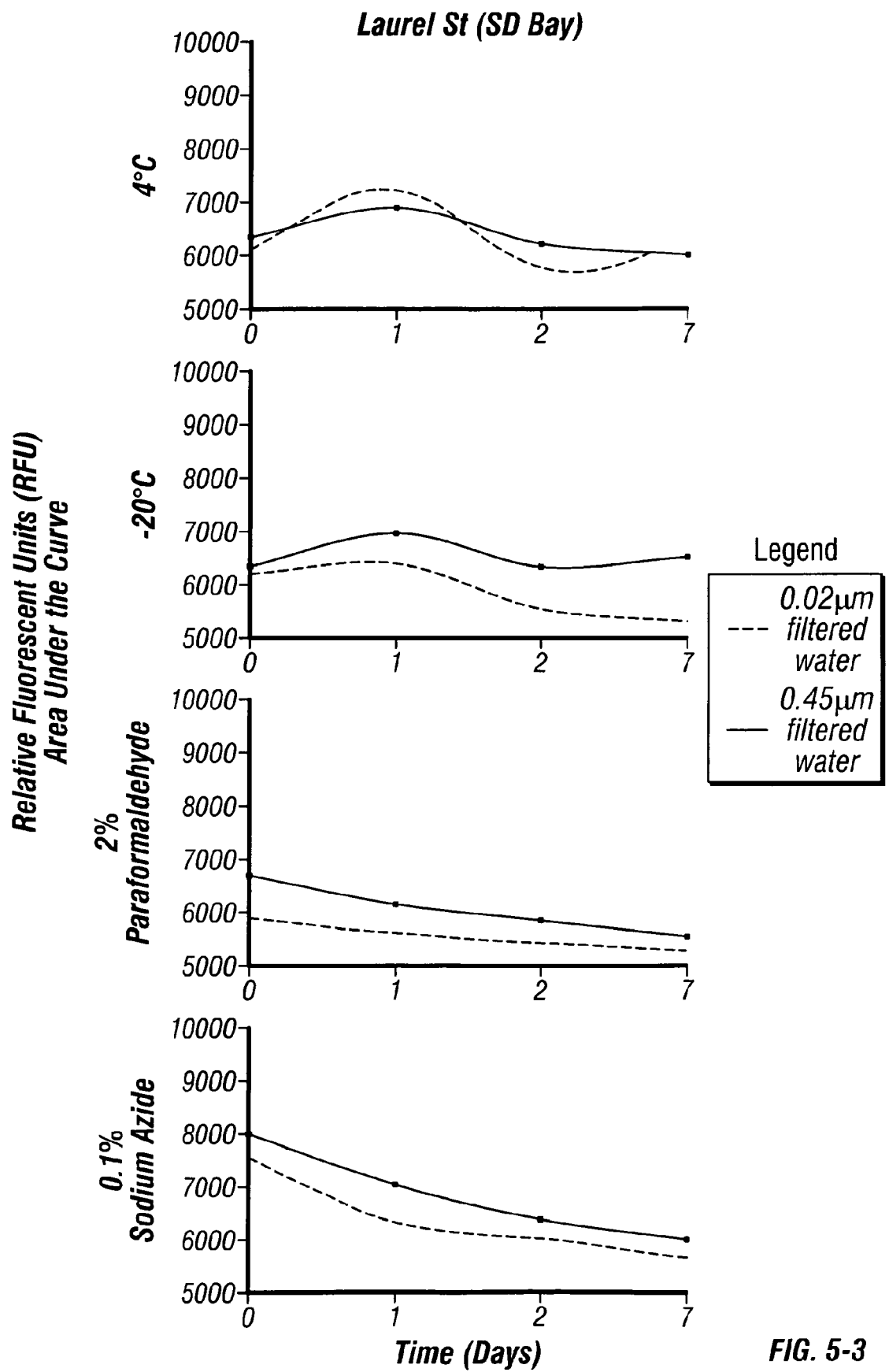

The Effects of Preservatives: To determine if the bulk fluorescence method was compatible with common preservation techniques, 3 different samples were harvested and stored at 4° C. or ~20° C. or treated with 2% paraformaldehyde or 0.1% sodium azide. As shown in FIG. 5, the differences in the RFUs for the Samples and Blanks were not consistent for any of the preservation techniques over time. Paraformaldehyde fixing seemed to be the best, but even those samples show variation over time. Other research has shown that microbial numbers, as determined by direct counts, can change over time even after the addition of preservatives (Wen et al., 2004). Therefore, samples should be analyzed as soon as possible in order to obtain the most accurate reading.

The Effects of High Versus Low DNA/RNA Content in Cells: Vibrio parahemalyticus was used to determine if there was a significant difference in the fluorescence of actively growing cells versus dormant cells. A high concentration sample ($\times10^7$ cells $ml^1$) and a low concentration sample ($\times10^6$ cells $ml^{-1}$) were both used for the comparison. Stationary cells had RFUs that were ~44% lower than those cells in log phase. Presumably, the extra fluorescence was due to higher RNA content. This implies that bulk fluorescence will be higher for actively growing microbial communities. In natural environments, ~50% of the microbes are categorized as high DNA/RNA content cells (Gasol et al., 1999). Therefore, in most environmental samples, the high and low DNA/RNA content cells would balance.

Recommended Protocol: Based on the results presented above, we suggest the following protocol. Syringe filter (0.45 μm for Sample and 0.02 μm for Blank) 1 ml of water sample into an eppendorf tube containing λ1 of 10,000X SYBR Gold and 13 units $ml.^{-1}$ of DNase I. Incubate for one minute. Measure the emission spectrum 450-650 λwith an excitation of 495 λ. Calculate area under the curve, $\Sigma([f(x_n)\Delta x - f(x_{n-1})\Delta x]/2)$. If a plate reading fluorometer is available, replicates should be measured and averages calculated. To calibrate the curve for a particular water type, initial direct counts with epifluorescent microscopy should be performed.

Measurement of Environmental Samples Using Recommended Protocol: Water samples were collected from freshwater and seawater in order to test the recommended protocol. Both freshwater and seawater fluorescent measurements showed a strong correlation, $r^2=0.96$ and 0.92 respectively, when compared to direct counts (Table 1). It can be concluded from these measurements that this bulk fluorescence method may be useful in estimating microbial abundances in both freshwater and seawater.

Approximation of Microbial Concentrations without Direct Counts: Table 2 represents a guide for estimating cell concentrations using relative measurements of similar water samples. This is only a guide for rapid approximations. Investigators should construct similar tables for their environment of choice.

Potential for Automation: An automated version of this protocol would need to include 0.45 and 0.02 μm filtration, an injection unit for mixing the SYBR® Gold and DNase I, a fluorometer, and a data recorder. Miniature fluorometers are commercially available (e.g., Ocean Optics; Dunedin, Fla.) and custom-built basic fluorometers are inexpensive to build. Such systems would be very good at estimating relative microbial concentrations. For example, most of the remote buoy systems for measuring total chlorophyll could be easily adapted to estimating microbial numbers using the bulk fluorescent method. Simple photomulipler tube-UV systems would be particularly useful for routine monitoring of aquaculture ponds or storm drains in a city. We need methods for remote sensing of microbial dynamics. Bulk fluorescence of SYBR® Gold, as presented here, is a reasonable candidate for estimating numbers because it is robust and it can be performed with very simple, cheap equipment.

Experimental Procedures

Water sampling: All water samples were collected from the San Diego area, including Mission Bay, San Diego Bay, La Jolla Shores, Imperial Beach (TB), Ocean Beach (OB), OB Estuary, Torrey Pines, Lake Lindo, Lake Murray, the Old Mission Dam and the San Diego River. Portions of each sample were put through a 0.45 μm or 0.02 μm pore syringe filter. The 0.45 µm filter removes protists and eukaryotic algae and was used as the Sample. The 0.02 µm filter removes the microbial cells and viral particles and was used as the Blank.

Staining with SYBR Gold and Bulk Fluorescent Measurements: Both a Hitachi f4500 (Schaumburg, Ill.) and a Gemini XS (Molecular Devices Corporation; Sunnyvale, Calif.) were used in these experiments. Water samples measured using the single-cell Hitachi fluorometer were prepared by mixing 1 ml of the Sample or the Blank with 1 µl 10,000×SYBR Gold nucleic acid stain (Molecular Probes; Eugene, Oreg.). The relative fluorescence was measured using an excitation wavelength of $495\lambda$ and an emission spectra ranging from $450$-$650\lambda$. For measurements using the Gemini fluorometer 1 µl of 10,000×SYBR Gold was added to 1 ml of Sample or Blank, then 200 µl aliquots were pipetted into 4 wells on a 96-well plate. The parameters set for the excitation and emissions wavelengths on the Gemini fluorometer were identical to those set on the Hitachi, except, a cut-off filter at $515\lambda$ was used. A cutoff filter was not available on the Hitachi, nevertheless, the emission curves generated by both fluorometers were similar.

Epifluorescence microscopy: Cells were counted by filtering samples fixed in 2% paraformaldehyde onto a 0.02 µm Anodisc (Whatman), staining with SYBR Gold (Molecular Probes, Inc), and directly counting by epifluorescent microscopy. Cells were visualized at 1000× using a Leica DM RBE microscope equipped for epifluorescence with a mercury bulb (100 W) and filter set XF57-1 (Omega). Images were captured using a CCD camera (Olympus America) and cells were counted (>200 per sample) in 10-20 fields selected at random.

Seawater Dilution Series: One liter of seawater was collected from the San Diego Bay. The seawater was 0.45 µm filtered and then diluted by 1/5, 2/5, 3/5, and 4/5 using 0.02 µm filtered seawater collected from the same site. One µl of 10,000×SYBR Gold DNA stain was added to 1 ml of each dilution. The whole seawater and the 4 seawater dilutions were measured for their total fluorescence using both the Hitachi f4500 fluorescence spectrophotometer and the Gemini XS fluorometer. The area of each scan, $\Sigma([f(x_n)\Delta x - f(x_{n-1})\Delta x]/2)$, was calculated for the diluted Samples and the Blank (1 ml of 0.02 µm filtered seawater). For the dilution series measured using the Gemini fluorometer, two-tailed t-tests were used to determine whether significant difference existed between the averages obtained from the four replicates measured per Sample and the percentage of bacteria in the Sample. Three ml of each dilution were also fixed in 2% paraformaldehyde and the microbes (>200 cells) were counted using epifluorescent microscopy.

Field Tests: Fifty ml water samples were collected from 6 different sites in San Diego, Calif. Samples were collected from Fiesta Island, San Diego Bay, Mission Bay, Point Loma, Ocean Beach Estuary, and the San Diego River. Each water sample was 0.45 µm syringe filtered to remove large particles and eukaryotic organisms. One µl of 10,000×SYBR Gold DNA stain was added to 1 ml of each Sample and measured for its total fluorescence using a Hitachi f4500 fluorescent spectrophotometer. The emission spectrum of $450$-$650\lambda$ was collected (excitation=$495\lambda$). After a water sample was scanned, it was immediately pipetted out of the cuvette, and fixed with 2% paraformaldehyde for the direct counts. The area of each wavelength scan was calculated for all water samples.

Precision: To measure the precision of the fluorescence spectrophotometer, water samples were collected from theshipyard at San Diego Bay, Harbor Island, and Shelter Island.

All three samples were 0.45 µm syringe filtered to remove large particles and eukaryotic organisms. One µl of 10,000× SYBR Gold was added to 1 ml of each seawater Sample. The three different water samples were measured 3 separate times for their total fluorescence using the Hitachi f4500 and counted three separate times using epifluorescent microscopy.

DNase I Treatments: Two µl of 6475 units $ml^{-1}$ DNase I (Sigma; St Louis, Mo.) was added to 1 ml of water sample and incubated for 5 minutes at room temperatures. Samples for this experiment were measured on the Gemini fluorometer. The relative fluorescence was estimated by calculating the area under the emission spectrum. Four replicates were measured per sample and averages were calculated.

Effects of Preservatives: To test the effects of different preservatives on the SYBR Gold bulk fluorescence method, water samples collected from 3 different sites were stored at 4° C., −20° C., treated with 2% paraformaldehyde, or 0.1% sodium azide. Fluorescence was measured at 0, 24, 48 hrs, and 1 week post-preservation using the Gemini fluorometer. The relative fluorescence was estimated by calculating the area under the emission spectrum. Four replicates were measured per sample and averages were calculated.

Quantity of Relative Fluorescence in Actively Growing Versus Dormant Cells: Vibrio parahemalyticus was used as a model to test the effects of cells with high DNA/RNA content versus low DNA/RNA content on our bulk fluorescence methods. An overnight culture of V. parahemalyticus was grown at 37° C. in LB broth. Three different dilutions of overnight were added to three flasks containing 250 ml of 0.2 µm filtered autoclaved seawater. Cells were grown at room temperature with aeration for 12 hours (high DNA/RNA content cells) and for 72 hours (low DNA/RNA content cells). Sub-samples were taken, dilutions were made, and cells were measured for their fluorescence on the Gemini fluorometer using the methods previously described. One ml of each sample dilution was fixed in 2% paraformaldehyde and counted using epifluorescent microscopy.

Preparation and Measurement of Samples Using "Recommended" Conditions: Four freshwater and seven seawater samples were collected from the San Diego area. Water samples were 0.45 µm filtered (Sample) and 0.02 µm filtered (Blank) as previously described. Two µl of 6475 units $ml^{-1}$ DNase I was added to one ml of both filter fractions per sample and incubated for 5 minutes. One µl of 10,000×SYBR Gold was added and water samples were measured using the Gemini fluorometer as previously described. The Relative Fluorescent Units (RFU) were generated by calculating the area under the emission spectrum and subtracting the background fluorescence generated from the Blank measurement. One ml of each water sample was fixed in 2% paraformaldehyde and counted using epifluorescent microscopy Acknowledgements This research was supported by the SPAWAR Systems Center San Diego Independent Research (IR) Program and the National Science Foundation Aquatic Phage Grant (NSF03-16518). The authors thank Mya Breitbart for her contributions to the project, Beltran Rodriguez-Brito for his expertise on the mathematical and statistical calculations, and Steve Barlow at the SDSU-EMF for help with the microscopy.

TABLE 1

Measurement of freshwater and seawater samples using recommended protocol.

| Water Source | RFU After Background Subtraction | Manual Cell Counts (*$10^6$) | Correlation Between RFU and Manual Counts |
|---|---|---|---|
| Freshwater | | | |
| Goldfish Pond, SDSU | 567 | 0.41 | $r^2 = 0.96$ |
| Lake Murray | 2298 | 1.72 | |
| Old Mission Dam, SD | 2428 | 1.81 | |
| Lake Lindo | 4666 | 2.80 | |
| Seawater | | | |
| Cortez St., IB | 1299 | 1.53 | $r^2 = 0.92$ |
| Camp Surf Jetty, IB | 1548 | 2.59 | |
| Seacoast Dr., IB | 1598 | 2.89 | |
| Tijuana Slough | 1790 | 3.58 | |
| Coronado Dog Beach | 1834 | 3.74 | |
| OB Dog Beach | 2055 | 5.54 | |
| Capistrano Wy., MB | 2276 | 5.08 | |

Freshwater samples were collected from 3 lakes and 1 stream all located in the San Diego (SD) area.
Seawater samples were collected from 4 open ocean locations in Imperial Beach (IB) and Coronado Island, as well as 3 bay locations (Tijuana Slough, Ocean Beach (OB), and Mission Beach (MB)).
Relative Fluorescent Units (RFU) after background substitution calculations were generated by subtracting the Sample measurement from the Blank measurement.
Manual cell counts were conducted using epifluorescent microscopy.
Correlation Between RFU and manual counts represents the $r^2$ value generated from the four freshwater samples and from the seven seawater samples.

TABLE 2

Estimates of a range of cell concentration based on relative fluorescent values from freshwater and seawater samples.

| RFU Range ($A_{sample}$-$A_{blank}$) | Cells ml$^{-1}$ low estimate | Cells ml$^{-1}$ high estimate |
|---|---|---|
| Freshwater | | |
| 300-1000 | 1.46E+05 | 6.64E+05 |
| 1000-2000 | 4.85E+05 | 1.33E+06 |
| 2000-3000 | 9.69E+05 | 1.99E+06 |
| 3000-4000 | 1.45E+06 | 2.65E+06 |
| 4000-5000 | 1.94E+06 | 3.32E+06 |
| Seawater | | |
| 300-1000 | 4.66E+05 | 2.59E+06 |
| 1000-2000 | 1.55E+06 | 5.18E+06 |
| 2000-3000 | 3.11E+06 | 7.77E+06 |
| 3000-4000 | 4.66E+06 | 1.04E+07 |
| 4000-5000 | 6.21E+06 | 1.29E+07 |

FIGURE LEGENDS

FIG. 1. Measurement of bulk fluorescence in seawater dilution series using the Hitachi and Gemini XS fluorometers. The relative fluorescence was measured on the Hitachi fluorescent spectrophotometer using an excitation wavelength of 495λ and an emission spectra ranging from 450-650λ. The area under the curve was calculated and a XY scatter plot was constructed (A). Correlation between bulk fluorescence and manual cell counts in the seawater dilution series (B). Measurement of relative fluorescence in a seawater dilution series using Gemini fluorometer (C). The bulk fluorescence was estimated by calculating the area under the emission spectrum and a bar graph was constructed. Four replicates per sample were measured and averages were calculated. Correlation between relative fluorescence and percentage of whole seawater in sample (D). The Gemini fluorometer had the capability of measuring several replicates simultaneously, while the Hitachi could only measure single-cells.

FIG. 2. Measurement of bulk fluorescence in six San Diego water samples. Samples were collected from Mission Bay (MB), Ocean Beach (OB) Estuary, Point Loma, San Diego (SD) Bay, and the San Diego River. Each water sample was measured for the total fluorescence using a Hitachi f4500 fluorescent spectrophotometer. The emission spectrum of 450λ-650λ was collected (excitation=495λ). The area of each wavelength scan was calculated for all water samples. After a water sample was scanned, it was immediately pipetted out of the cuvettes and fixed with 2% paraformaldehyde for the direct counts by microscopy.

FIG. 3. Precision of the measurements for relative fluorescence in three seawater samples using Hitachi fluorescent spectrophotometer. The standard deviation in RFUs for the three samples ranged from 12 to 18. Estimates of total microbial numbers using epifluorescent microscopy ranged from $9.1 \times 10^5$ to $1.0 \times 10^6$ and the standard deviation ranged from $7.2 \times 10^4$ to $1.3 \times 10^5$. The average error using the fluorometer was 3.3%, while the average error for manual counts was 11%.

FIG. 4. The effects of DNase I on the relative fluorescence of seawater samples. Five water samples were treated with DNase I and compared to untreated samples with the bulk fluorescence protocol. The 0.02 and 0.45 µm filtered curves represent averages of four replicates.

FIG. 5. The effects of preservatives on seawater samples. Three seawater samples were stored at 4° C., −20° C., treated with 2% paraformaldehyde, or 0.1% sodium azide. Fluorescence was measured at 0, 24, 48 hrs, and 1 week post-preservation using the Gemini fluorometer.

REFERENCES

Boehme, J., Frischer, M. E., Jiang, S. C., Kellogg, C. A., Pichard, S., Rose, J. B. et al. (1993) Viruses, bacterioplankton, and phytoplankton in the southeastern Gulf of Mexico: distribution and contribution to oceanic DNA pools. *Mar Ecol Prog Ser* 97: 1-10.

Breitbart, M., Wegley, W., Leeds, S., Schoenfeld, T., and Rohwer, F. (2004) Phage community dynamics in hot springs. *Appl Environ Microbiol* 70: 1633-1640.

DeFlaun, M. F., Paul, J. H., and Jeffrey, W. H. (1987) Distribution and molecular weight of dissolved DNA in subtropical estuarine and oceanic environments. *Mar Ecol Prog Ser* 38: 65-73.

Gasol, J. M., Zweifel, U. L., Peters, F., Fuhrman, J. A., and Hagstrom, A. (1999) Significance of size and nucleic acid content heterogeneity as measured by flow cytometry in natural planktonic bacteria. *Appl Environ Microbiol* 65: 4475-4483.

Hobbie, J. E., Daley, R. J., and Jasper, S. (1977) Use of nuclepore filters for counting bacteria by epifluorescence microscopy. *Appl Environ Microbiol* 33: 1225-1228.

Jiang, S. C., and Paul, J. H. (1995) Viral contribution to dissolved dna in the marine environment as determined by differential centrifugation and kingdom probing. *Appl Environ Microbiol* 61: 317-325.

Noble, R. T., and Fuhrman, J. A. (1998) Use of SYBR Green I for rapid epifluorescence counts of marine viruses and bacteria. *Aquat Microb Ecol* 14: 113-118.

Paul, J. H., Jeffrey, W. H., and DeFlaun, M. F. (1987) Dynamics of extracellular DNA in the marine environment. *Appl Environ Microbiol* 53: 170-179.

Wen, K., Ortmann, A. C., and Suttle, C. A. (2004) Accurate estimation of viral abundances by epifluorescence microscopy. *Appl Environ Microbiol* 70: 3862-3867.

What is claimed is:

1. A method for remote enumerating of microbial cells in a sample using a multiplexed high through-put system designed for remote measuring of total fluorescence of the sample to estimate the number of cells in the sample, the method comprising the following steps:
   (a) providing a multiplexed high through-put system designed for remote measuring of total fluorescence of the sample, a fluorescent cyanine nucleic acid stain, a DNase I, and a liquid or a water sample, wherein the multiplexed high through-put system comprises:
   at least one sample holding unit, mixing unit and injection unit,
   at least two low protein binding filters for filtering the samples, wherein the system comprises at least one 0.45 µm low protein binding filter for samples and at least one 0.02 µm low protein binding filter for blanks,
   an injection unit for injecting into the mixing unit the cyanine nucleic acid stain and DNase I, wherein the mixing unit mixes the cyanine nucleic acid stain and DNase I, or the injection unit injects and mixes the cyanine nucleic acid stain and DNase I,
   a sample processor for inputting samples into the fluorometer,
   a fluorometer,
   a data recorder,
   a data output device for outputting to a user a total fluorescence, and
   a computer system for calculating a total fluorescence;
   (b) filtering the liquid or water sample, and a liquid or water blank, with at least one low protein binding filter, wherein the 0.45 µm filter filters samples and the 0.02 µm filter filters blanks;
   (c) adding the DNase I and the fluorescent cyanine nucleic acid stain, or equivalent, to the filtered sample and filtered blank,
   wherein the mixing unit mixes the cyanine nucleic acid stain and DNase I, or the injection unit injects and mixes the cyanine nucleic acid stain and DNase I;
   (d) measuring a total bulk fluorescence in the sample and the blank,
   wherein the total fluorescence is measured using an excitation wavelength of 495 lambda and an emission spectra ranging from 450 to 650 lambda;
   (e) outputting to a user by the data output device the measured total fluorescence; and
   (f) calculating using the computer system the total fluorescence by comparing the measured total fluorescence in the 0.45 µm filtered cell-comprising sample with the 0.02 µm filtered blank control sample, and determining the estimate of the total number of microbial cells in the sample by correlating the total fluorescence to a standard sample measurement.

2. The method of claim 1, wherein (i) the low protein binding filter comprises a polycarbonate filter, a polyvinylidenedifluoride (PVDF) filter or equivalent; or (ii) the method of (i), wherein the polyvinylidenedifluoride (PVDF) filter comprises a hydrophilic PVDF filter.

3. The method of claim 1, wherein the sample filtration further comprises use of a 0.30 µm filter, 0.35 µm filter, 0.40 µm filter, a second 0.45 µm filter, a 0.50 µm filter or a 0.55 µm filter.

4. The method of claim 1, wherein the liquid or water sample is diluted before filtering, after filtering or both before and after filtering.

5. The method of claim 4, wherein the liquid or water sample is treated with the DNase I before filtering, after filtering or both before and after filtering, or before dilution, after dilution or both before and after dilution.

6. The method of claim 1, wherein the total fluorescence in the sample is measured with a fluorescent spectrophotometer.

7. The method of claim 1, further comprising use of a kit comprising: (i) solutions for practicing the method of claim 1; or (ii) the kit of (i) wherein the kit further comprises instructions for practicing the method of claim 1.

8. The method of claim 1, wherein the multiplexed high through-put system further comprises a computer system and data output device for calculating and outputting to a user a total fluorescence and a relative fluorescence unit (RFU), wherein the Relative Fluorescent Units were generated by calculating area under an emission spectrum and subtracting background fluorescence generated from the Blank measurement.

9. The method of claim 1, wherein the sample is an environmental sample.

10. The method of claim 9, wherein the environmental sample provided in the form of a liquid solution comprises a biological, a soil or a water sample.

11. The method of claim 10, wherein the water sample comprises water from a salt water, hot spring, public water supply, water tank, reservoir, fresh water, aquifer, storm drain, river, lake or aquaculture pond water source.

12. The method of claim 10, wherein the biological sample comprises a plant, seed or an animal tissue sample.

13. The method of claim 1, wherein the liquid comprises a starting material of an initial non-liquid sample mixed with an aqueous solution or a liquid.

* * * * *